United States Patent
Aksu

(10) Patent No.: US 11,737,879 B2
(45) Date of Patent: Aug. 29, 2023

(54) SACROILIAC JOINT IMPLANTS AND IMPLANTATION METHODS

(71) Applicant: Kenan Aksu, Exton, PA (US)

(72) Inventor: Kenan Aksu, Exton, PA (US)

( * ) Notice: Subject to any disclaimer, the term of this patent is extended or adjusted under 35 U.S.C. 154(b) by 628 days.

(21) Appl. No.: 16/514,468

(22) Filed: Jul. 17, 2019

(65) Prior Publication Data

US 2019/0336292 A1     Nov. 7, 2019

Related U.S. Application Data

(63) Continuation of application No. 16/008,173, filed on Jun. 14, 2018, now Pat. No. 10,357,368, which is a continuation of application No. 14/518,667, filed on Oct. 20, 2014, now abandoned.

(60) Provisional application No. 61/893,027, filed on Oct. 18, 2013.

(51) Int. Cl.
  *A61F 2/30* (2006.01)
  *A61B 17/68* (2006.01)
  *A61B 17/16* (2006.01)

(52) U.S. Cl.
  CPC ........... *A61F 2/30* (2013.01); *A61B 17/68* (2013.01); *A61B 17/1659* (2013.01); *A61F 2002/30622* (2013.01); *A61F 2002/30995* (2013.01)

(58) Field of Classification Search
  CPC .. A61F 2002/30995; A61F 2002/30622; A61F 2/30; A61F 2/447; A61B 17/68
  See application file for complete search history.

(56) References Cited

U.S. PATENT DOCUMENTS

| | | | | |
|---|---|---|---|---|
| 5,242,444 A | * | 9/1993 | MacMillan | A61B 17/7055 606/86 R |
| 6,053,916 A | * | 4/2000 | Moore | A61F 2/30988 606/86 R |
| 6,235,059 B1 | * | 5/2001 | Benezech | A61F 2/447 606/247 |
| 6,682,563 B2 | * | 1/2004 | Scharf | A61F 2/4455 606/247 |
| RE38,614 E | * | 10/2004 | Paul | A61F 2/4455 623/925 |
| 8,221,428 B2 | | 7/2012 | Trieu | |
| 8,343,189 B2 | | 1/2013 | Assell et al. | |
| 8,348,950 B2 | | 1/2013 | Assell et al. | |
| 8,690,928 B1 | * | 4/2014 | Walkenhorst | A61F 2/4455 606/287 |
| 8,808,377 B2 | | 8/2014 | Donner | |
| 8,945,227 B2 | * | 2/2015 | Kirschman | A61B 17/70 623/17.16 |
| 8,979,928 B2 | | 3/2015 | Donner | |

(Continued)

*Primary Examiner* — Ellen C Hammond
(74) *Attorney, Agent, or Firm* — Offit Kurman, P.A.; Gregory A. Grissett

(57) ABSTRACT

Sacroiliac (SI) joint implants for promoting SI joint fusion and methods of their delivery are described herein. The SI joint implant has a spacer operatively coupled to a planar member having tapered holes to receive fastening elements. When placed in the SI joint, the spacer engages the articular surfaces of the SI joint while the plate traverses the SI joint. The implant is held in place fastening elements, which are inserted through the tapered holes in the planar member. The implant is delivered via an inferior inlet MIS procedure, wherein the SI joint is accessed through an inlet inferior to the SI joint.

18 Claims, 14 Drawing Sheets

(56) References Cited

U.S. PATENT DOCUMENTS

| | | |
|---|---|---|
| 9,119,732 B2 | 9/2015 | Schifano et al. |
| 9,186,155 B2 | 11/2015 | Katzman et al. |
| 10,045,797 B1* | 8/2018 | Walkenhorst ........... A61F 2/447 |
| 10,603,187 B2* | 3/2020 | Laubert ............... A61F 2/30942 |
| 2002/0016592 A1* | 2/2002 | Branch ............ A61B 17/1671 |
| | | 606/279 |
| 2002/0107574 A1* | 8/2002 | Boehm, Jr. ........... A61F 2/4611 |
| | | 623/17.16 |
| 2002/0138146 A1* | 9/2002 | Jackson ................ A61F 2/4455 |
| | | 623/17.11 |
| 2005/0071008 A1* | 3/2005 | Kirschman ............. A61F 2/447 |
| | | 606/328 |
| 2005/0101960 A1* | 5/2005 | Fiere .................... A61F 2/4611 |
| | | 623/17.11 |
| 2005/0159813 A1* | 7/2005 | Molz .................... A61F 2/4611 |
| | | 623/17.11 |
| 2008/0294262 A1* | 11/2008 | Levieux ................ A61F 2/4611 |
| | | 606/280 |
| 2009/0216238 A1* | 8/2009 | Stark .................... A61F 2/4657 |
| | | 606/329 |
| 2009/0326580 A1* | 12/2009 | Anderson .......... A61B 17/8047 |
| | | 606/301 |
| 2010/0268228 A1* | 10/2010 | Petersen ............ A61B 17/1757 |
| | | 606/60 |
| 2011/0060375 A1* | 3/2011 | Bonutti .................. A61L 27/58 |
| | | 606/86 A |
| 2011/0238181 A1* | 9/2011 | Trieu ................. A61B 17/7055 |
| | | 623/17.11 |
| 2011/0264229 A1* | 10/2011 | Donner ................ A61F 2/4611 |
| | | 623/18.11 |
| 2012/0022535 A1* | 1/2012 | Mayer .................. A61F 2/4611 |
| | | 606/1 |
| 2012/0095560 A1* | 4/2012 | Donner ................ A61F 2/4455 |
| | | 623/17.11 |
| 2012/0296428 A1 | 11/2012 | Donner |
| 2012/0316565 A1 | 12/2012 | Stark |
| 2013/0035723 A1 | 2/2013 | Donner |
| 2013/0060337 A1* | 3/2013 | Petersheim .......... A61B 17/809 |
| | | 623/17.16 |
| 2014/0012380 A1* | 1/2014 | Laurence ................ A61F 2/447 |
| | | 623/17.16 |
| 2014/0088707 A1 | 3/2014 | Donner et al. |
| 2014/0107786 A1* | 4/2014 | Geisler ............... A61F 2/30965 |
| | | 623/17.16 |
| 2014/0135927 A1* | 5/2014 | Pavlov .................. A61F 2/4455 |
| | | 623/17.11 |
| 2014/0200618 A1* | 7/2014 | Donner ................. A61F 2/4611 |
| | | 606/281 |
| 2014/0207240 A1* | 7/2014 | Stoffman ................ A61B 17/68 |
| | | 623/18.11 |
| 2014/0228960 A1* | 8/2014 | Forterre .................. A61F 2/442 |
| | | 623/17.16 |
| 2015/0073486 A1 | 3/2015 | Marotta et al. |
| 2015/0073488 A1* | 3/2015 | Rinner ............... A61B 17/7076 |
| | | 606/305 |
| 2015/0112444 A1* | 4/2015 | Aksu ......................... A61F 2/30 |
| | | 623/18.11 |
| 2015/0173805 A1* | 6/2015 | Donner .................. A61B 17/68 |
| | | 606/279 |
| 2015/0182268 A1* | 7/2015 | Donner ............. A61B 17/1757 |
| | | 606/291 |
| 2015/0209087 A1 | 7/2015 | Donner |
| 2015/0250612 A1 | 9/2015 | Schifano et al. |
| 2015/0335372 A1 | 11/2015 | Schifano et al. |
| 2016/0058480 A1* | 3/2016 | Laubert ............... A61B 17/808 |
| | | 606/281 |
| 2016/0235546 A1* | 8/2016 | Cheng ..................... A61F 2/446 |
| 2016/0367379 A1* | 12/2016 | Refai ....................... A61F 2/447 |
| 2018/0360608 A1 | 12/2018 | Aksu |
| 2019/0365542 A1* | 12/2019 | Tyber ..................... A61L 31/18 |
| 2020/0155324 A1* | 5/2020 | Sazy ..................... A61F 2/30771 |
| 2020/0281736 A1* | 9/2020 | Milz .................... A61B 17/8042 |
| 2021/0045892 A1* | 2/2021 | Rogers ................. A61F 2/30749 |
| 2021/0322181 A1* | 10/2021 | Predick ................... A61F 2/447 |

* cited by examiner

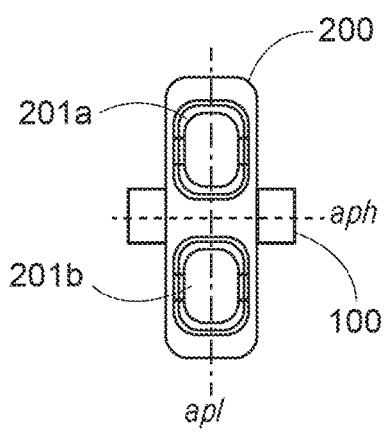
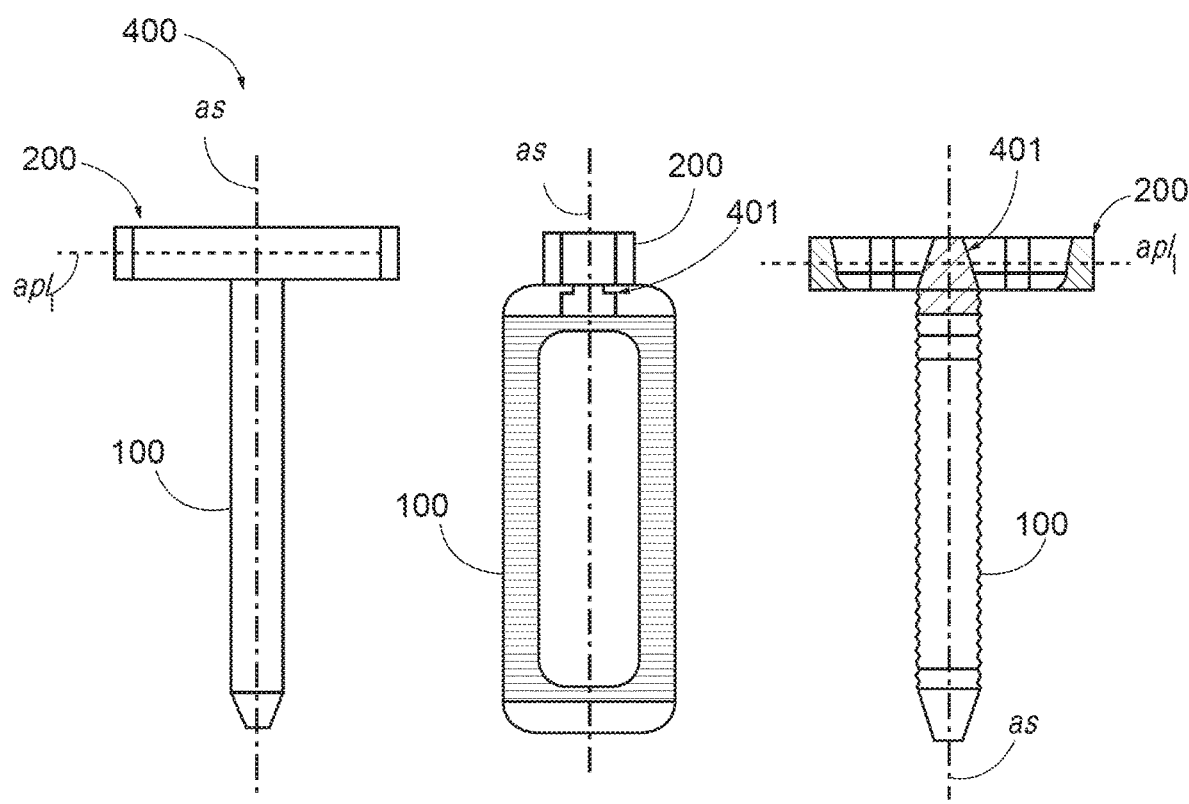
FIG. 4A
FIG. 4B  FIG. 4C  FIG. 4D

SACROILIAC JOINT IMPLANTS AND IMPLANTATION METHODS

CROSS REFERENCE TO RELATED APPLICATIONS

This application is a continuation of U.S. application Ser. No. 16/008,173, filed Jun. 14, 2018, which is a continuation of U.S. application Ser. No. 14/518,667, filed Oct. 20, 2014, which claims priority to and the benefit of U.S. Provisional Application Ser. No. 61/893,027 filed on Oct. 18, 2013, the contents of which are hereby incorporated in their entirety.

FIELD OF THE INVENTION

The present invention relates generally to surgical procedures for a sacroiliac (SI) joint, and more specifically, to SI joint implants and minimally invasive surgical (MIS) procedures for delivering SI joint implants.

BACKGROUND OF THE INVENTION

Sacroiliac (SI) joints are located between the sacrum and the right and the left iliac bones, respectively. The SI joints provide support for the entire weight of the upper body when a human stands erect, which creates a large amount of stress on the SI joints. Therefore, these joints are susceptible to injury and degeneration. Acute and chronic injury, degeneration, and laxity of the supporting ligaments of the SI joint can result in low back and radiating buttock and leg pain in afflicted patients. Stabilization or immobilization (fixation) of the SI joint is commonly advocated as a surgical treatment for many SI joint disorders.

A significant problem with certain conventional methods for SI joint fixation is that they require a surgeon to have direct access and a view of the SI joint. Thus, some conventional SI joint fixation techniques require the use of what is commonly referred to as "open surgery," and result in significant trauma and disruption to the tissues and skin surrounding the SI joint. Open procedures increase the risk of damage to major nerves, blood vessels, ligaments, and muscles around the incision site. Moreover, open procedures increase operative, hospitalization, and recovery time due to the extensive soft tissue damage resulting from open surgery techniques.

In response to the problems related to open surgery for SI joint fixation, minimally invasive surgical (MIS) procedures were developed. Currently, one of two approaches is taken to access the SI joint for fixation procedures: a lateral approach and a posterior approach. In conventional MIS procedures employing the lateral approach, screws, rods, or other fixation devices are passed through a small incision (as compared to that in open surgery) made on the lateral hip and inserted laterally through the ilium, across the SI joint space, and into the sacrum. See, e.g. U.S. Pat. No. 8,221,428 by Trieu.

Alternatively, a posterior approach may be used to access the SI joint for delivery of SI joint implants. See, e.g. U.S. Publication No. 2012/0316565 by Stark and U.S. Publication No. 2013/0035723 by Donner. In the posterior approach disclosed by Stark and Donner a small (as compared to that in open surgery) incision made in the patient's back, and the SI joint is accessed through an extra-articular recess located between the sacrum and the ilium.

Although the points of incision are different in current MIS procedures for accessing the SI joint, neither is truly minimally invasive. Conventional lateral MIS procedures still may result in significant trauma to the major nerves, blood vessels, and muscle groups of the hip. While current posterior MIS approaches eliminate damage to the soft tissues and neurovascular system of the lateral hip, they still carry a significant risk of trauma to the spinal nerves and major back and hip ligaments.

There exists a need for improved MIS procedures and devices that are less invasive and decrease soft tissue trauma and the risk to neurovascular tissue during SI joint fixation procedures.

Therefore, it is an object of the invention to provide an improved, less invasive method for implanting a fixation device in the SI joint.

It is further an object of the invention to provide an improved SI joint implant device with decreased risk of trauma to surrounding tissues during implantation.

SUMMARY OF THE INVENTION

Implants for fixation of the SI joint, kits containing the implants, and methods of using the implants and kits are described herein. In the methods, the sacroiliac (SI) joint implant is implanted in the SI joint using a minimally invasive surgical (MIS) technique that accesses the SI joint via an inferior inlet approach. The inferior inlet approach provides a less invasive and safer approach for delivery of a SI joint implant than current methods. Preferably, the SI joint implant includes a spacer operatively coupled to a planar member having tapered holes to receive fastening elements. When delivered to the SI joint, the spacer engages the articular surfaces of the SI joint, which distracts the SI joint providing stabilization of the hypermobile SI joints, while the planar member traverses the SI joint providing static stabilization. The implant is fixed within the SI joint by fastening elements, which are inserted through the tapered holes of the planar member.

In one embodiment the spacer is operatively coupled to the planar member in situ during an implantation procedure. In an alternative embodiment, the spacer is operatively coupled to the planar member ex vivo and is delivered to the SI joint as a single unit. In further embodiments, the planar member is curved so as to conform to the contour of the ilium.

BRIEF DESCRIPTION OF THE DRAWINGS

FIGS. 4A-4D show several views of one embodiment of a SI joint implant assembled ex vivo.

DETAILED DESCRIPTION OF THE INVENTION

The following discussion includes a description of a joint implant system, related components, and exemplary methods of employing the implant system. Generally, FIGS. 1A-7D and 10A-11C illustrate several embodiments of the disclosed SI implant system. FIGS. 8-9 and 16-17 illustrate the use of the several embodiments illustrated in FIGS. 1A-7D and 10A-11C in a patient in need of SI joint fixation. FIGS. 12-15 illustrate exemplary tools for preparing the SI joint space for receiving a SI joint implant. While several embodiments are described in connection with these drawings, there is no intent to limit the disclosure to the embodiment or embodiments illustrated therein.

I. Sacroiliac Implant System

The SI implant system has a spacer, which serves as a medium to stabilize and promote bone growth in the SI joint to promote SI joint fusion.

The spacer contains or is operatively coupled to one or more stabilizing elements. The spacer is operatively coupled to a planar member having a tapered hole or holes. The planar member is fixed to the sacrum and ilium and holds the spacer in place within the SI joint while new bone growth occurs. Although it is not a requirement, the planar member may also provide compression across the SI joint.

a. Spacer

Figure 1A:
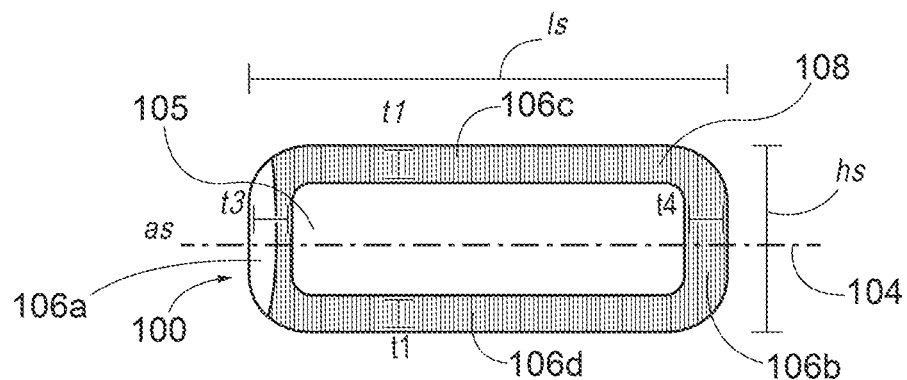
FIGS. 1A-1C show several views of one embodiment of a spacer configured for use in a SI joint implant.
Figure 1B:
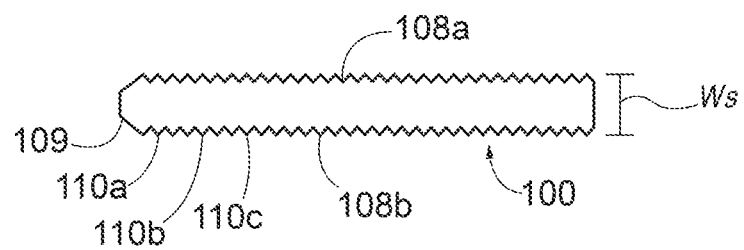
Figure 1C:
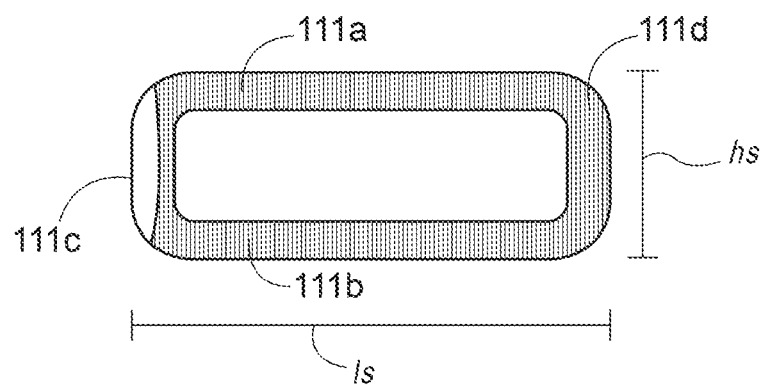

The spacer 100 is an elongated member having a length ls, a height hs, and a width ws. An exemplary spacer is depicted in FIGS. 1A-1C. The spacer 100 has a first longitudinal axis as, which extends along the length ls of the spacer 100. The spacer 100 serves as a medium for bone growth to promote fusion of the SI joint.

The length ls of the spacer 100 ranges from approximately 30 mm to approximately 50 mm. The height hs of the spacer 100 ranges from approximately 15 to approximately 25 mm. The width ws of the spacer 100 ranges from approximately 6 mm and approximately 8 mm. Insofar as the SI joint is a longitudinal joint, it is not a requirement that the spacer 100 conform exactly to the dimensions of the SI joint space. In some embodiments, the spacer 100 may be smaller than the joint space. In other embodiments the spacer 100 is substantially the same size as the joint space. In yet further embodiments the spacer 100 may be larger than the joint space. Most preferably the width ws of the spacer is approximately 2 mm larger than the width of a box chisel (1300, FIG. 13) that is used to prepare the SI joint space. A spacer 100 that is wider than the prepared SI joint space provides a press-fit and distracts the SI joint to increase stabilization of the SI joint. Preparation of the SI joint space is discussed in greater detail below.

Preferably, the spacer 100 is provided in three sizes: small, medium, and large, which can be provided together in a kit. Each size is suitable for use with patients of a particular range of body sizes. For example, the small spacer is suitable for use in people shorter than approximately 5'0", the medium spacer is suitable for people between approximately 5'0" and 6'0", and the large spacer is suitable for people taller than approximately 6'0". Patient ranges for spacer sizes can be determined using other parameters, such as body weight and pelvis size. Preferably, the small spacer has a length ls of 20 mm, a height hs of 15 mm and a width ws of 8 mm. Preferably, the medium spacer has a length ls of 25 mm, a height hs of 17 mm and a width ws of 8 mm. Preferably, the large spacer has a length ls of 30 mm, a height hs of 20 mm and a width ws of 8 mm.

The spacer 100 typically has four sides 111a, 111b, 111c, and 111d, (collectively 111) of the spacer 100. In some embodiments, all four sides 111 are equal. In other embodiments, no two sides 111 are equal. Preferably, two sides (e.g. 111a and 111b) are equal to each other, but longer than the other two sides (e.g. 111c and 111d). In this embodiment, the two shorter sides (e.g. 111c and 111d) are equal to each other. See e.g. FIG. 1C.

In the preferred embodiment, the spacer 100 has a cavity 105. The cavity 105 is configured to receive materials suitable for facilitating joint fusion. For example, bone graft material may be placed within the cavity 105 to promote joint fusion. The cavity 105 creates spacer edges 106a, 106b, 106c, and 106d (collectively 106) each having a thickness t1-t4. Preferably, the cavity 105 is configured such that the cavity 105 is maximized while not compromising the structural integrity of the spacer 100.

In some embodiments, t1-t4 are substantially equal to one another. For these embodiments t1-t4 ranges from approximately 2 mm to approximately 4 mm. In further embodiments, t1-t4 vary such that no two thicknesses are substantially the same. In these embodiments, t1-t4 ranges from approximately 2 mm to approximately 6 mm.

In a preferred embodiment, t1 and t2 are substantially equal, ranging from approximately 2 mm to approximately 4 mm. Also, in the preferred embodiment, t3 and t4 are substantially equal, ranging from approximately 3 mm to approximately 5 mm.

In a preferred embodiment t1 and t2 are substantially different from t3 and t4. Most preferably, t1 and t2 are less than t3 and t4, wherein t3 and t4 range from approximately 3 mm to approximately 6 mm. This embodiment is shown in FIG. 1A.

i. Structural Surface Configurations

In some embodiments, a surface 108a and 108b (collectively 108) of the spacer 100 is configured to aid in SI joint fixation and implant integration within the SI joint. For example, as shown in FIG. 1B, in one embodiment, opposing surfaces 108 of the spacer 100, which engage the articular surfaces of the SI joint in vivo, are configured to have ridges 110a, 110b, 110c (collectively 110). The ridges 110 may be uniform or may vary in width and depth along the length is of the spacer 100. In other embodiments, the ridges 110 may be spikes or other projections out of the surface 108.

Further embodiments of the spacer 100 have a tapered edge 109. In some instances, the tapered edge 109 has a suitable shape and size to improve implant fit within the SI joint. The taper may have structural configurations, such as ridges 110.

In some embodiments, such as embodiments configured for in situ assembly, the spacer 100 is operatively coupled to the planar member (FIG. 2A-2C) via an assembly element (FIG. 3, 303), preferably a cam assembly. In these embodiments, the spacer 100 also has a first assembly hole (FIG. 3, 301) that is preferably located on a short side (111c or 111d) of the spacer 100. Most preferably, the first assembly hole (301) is located on the first longitudinal axis as, which is equidistant from either end (602a and 602b) of the short side (111c or 111d). See e.g. FIGS. 6C and 6D. In other embodiments, the first assembly hole (301) is placed on a long side (111a or 111b) of the spacer 100. One having ordinary skill will appreciate that the exact location of the first assembly hole (301) will depend on, inter alia, the joint involved, type of injury, and treatment desired. For example, the orientation of the spacer within the SI joint will determine if the first assembly hole is more appropriate on a short side (111c or 111d) or long side (111a or 111b) of the spacer 100.

Other structural surface modifications may be used as deemed necessary or preferred. It will be appreciated by one having ordinary skill that the type of structural surface modification is dependent, inter alia, such as joint region involved, type of injury, and treatment desired.

ii. Bioactive Factors

A wide range of bioactive factors can be applied in the form of a coating or otherwise integrated into the surface of the spacer or planar member to aid in SI joint fixation by inducing and supporting healing, repair and regeneration of soft and hard tissue, in particular, bone and cartilage. Suitable factors include, but are not limited to, autologous bone from ipsilateral posterior superior iliac spine, nucleotides, peptides, proteins, antibodies, biocompatible chemical compounds, and other pharmaceuticals. Preferred bioactive factors include parathyroid hormones (PTHs), platelet-derived growth factors (PDGFs), Transforming growth factor betas (TGF .beta.s), bone morphogenetic proteins (BMPs), vascular endothelial growth factor (VEGFs), Insulin-like growth factors (IGFs), Fibroblast Growth Factors (FGFs), and variants having the same effect in the human or animal body. Most preferred bioactive factors include autologous bone graft, PDGF AB, PTH1-34, BMP2, BMP 7, TGF beta 1, TGF beta 3, VEGF 121, and VEGF 110. Other suitable bioactive factors include, but are not limited to, antibiotics, chemotherapeutics, analgesics, anesthetics, anti-proliferating agents, and immunomodulators.

a. Planar Member i. Straight Planar Member

Given the irregular and substantially curved structure of the sacrum and the ilium on either side of the SI joint, a substantially straight planar member (planar member) is preferably configured so as to prevent undesired contact with the sacrum or ilium. Thus, preferably a planar member is just large enough to accommodate two tapered holes.

Figure 2A:
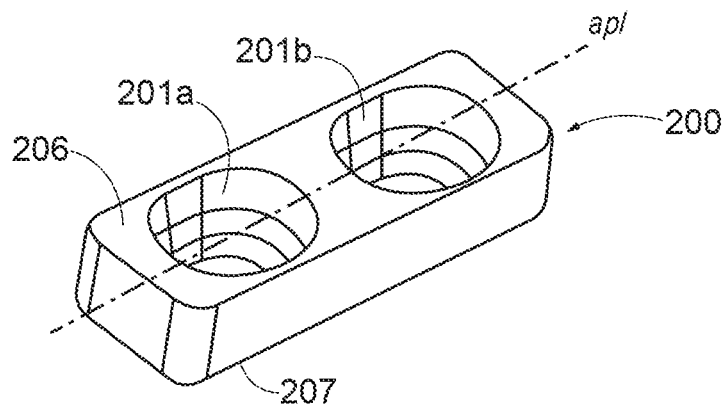
FIGS. 2A-2C show several views of one embodiment of a planar member having a tapered hole for use in a SI joint implant.
Figure 2B:
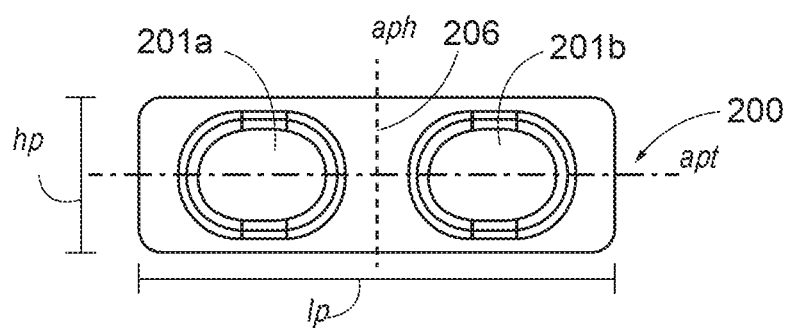
Figure 2C:
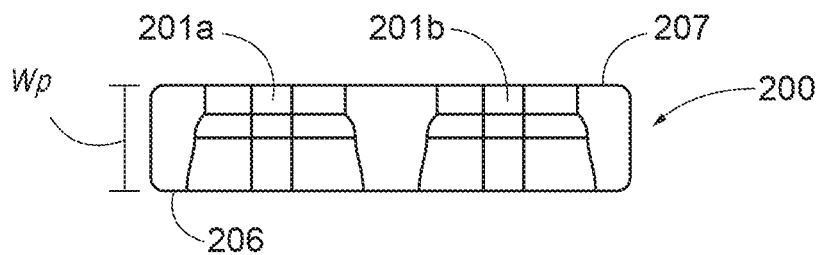

FIGS. 2A-2C show several views of one embodiment of a planar member 200 having a tapered hole 201 for use in a SI joint implant. In one embodiment, the planar member 200 has a length 1 along a second longitudinal axis a, a height h, and a width 2. In the preferred embodiment, the planar member 200, has two tapered holes 201a and 201b (collectively 201) for receiving a fastening element (601a and 601b, collectively 601, FIG. 6). Other embodiments contain additional holes 201, if additional fastening elements (601) are used. One having ordinary skill will appreciate that the number of fastening elements required depends on, inter alia, the joint involved, type of injury, and treatment desired. The tapered holes may be off-set from one another so as to decrease the length lp of the planar member 200.

As shown in FIG. 2C, the tapered hole 201 is tapered along the width wp of the planar member 200. Thus, the first opening of the tapered hole 201 on a top surface 206 of the planar member 200 is larger than the second opening of the tapered hole on a bottom surface 207 of the planar member 200. The tapered hole 201 has any suitable shape, including but not limited to, substantially circular, elliptical, oblong, irregular, and rectangular. Preferably, the tapered hole 201 is oblong. Preferably, the diameter of the tapered hole is approximately 4 mm to approximately 6 mm. By way of example, the planar member 200 can be an AO Foundation compression plate.

In some embodiments, such as embodiments configured for in situ assembly, the planar member 200 is operatively coupled to the spacer 100 (FIG. 1A-1B) via an assembly element (303), preferably a cam assembly. In these embodiments, the planar member 200 also has a second assembly hole (FIG. 3, 302) that is preferably located on the planar member 200 such that it is centered along a horizontal axis aph and extends through the entire width wp of the planar member 200. For all embodiments, the second assembly hole (302) is located at any position along the second longitudinal axis apl that is not occupied by a tapered hole 201. See e.g. FIG. 3.

One having ordinary skill will appreciate that the exact location of the second assembly hole (302) will depend, in part, on the number of fastening elements (601) required. The number of holes is equivalent to the number of fastening elements (601).

ii. Curved Planar Member

Figure 5A:
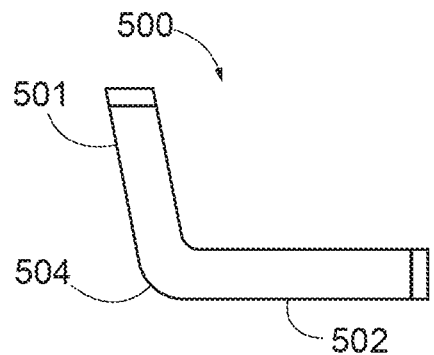
FIG. 5A shows one view of a curved planar member.
Figure 5B:
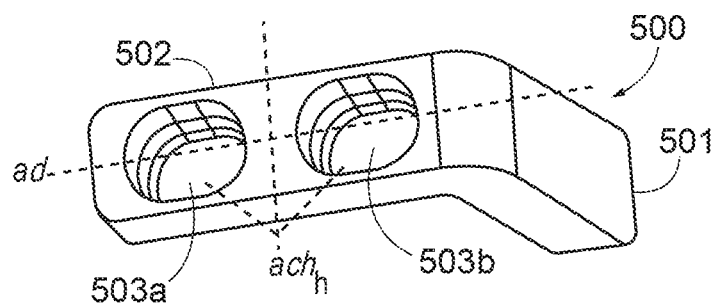
FIGS. 5B and 5C show two different embodiments of the curved planar member of FIG. 5A.
Figure 5C:
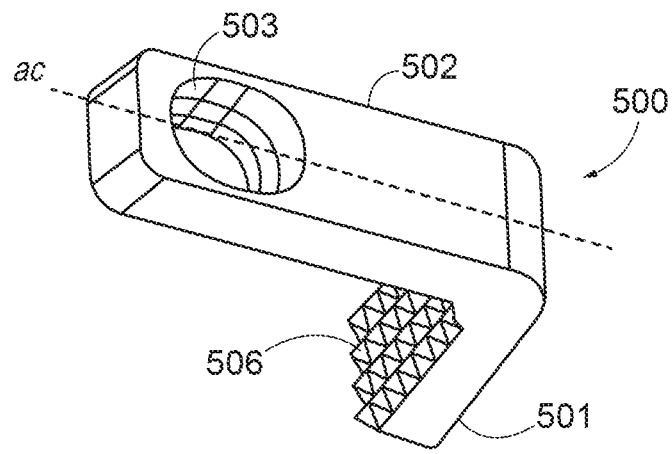

FIGS. 5A-5C shows several views of a curved member having a tapered hole for use in a SI joint implant. The sacrum and ilium are substantially irregular in shape and contour. In particular, they both have a substantial curve in the bone in close proximity of the SI joint. This presents challenges for affixing implants in this region. Thus, in some embodiments, the SI joint implant is a curved planar member 500 that matches the contour of the ilium. In other embodiments, the curved planar member 500 matches the contour of the sacrum. To match the contour of the sacrum, the curved planar member 500 has a curve ranging from approximately 30 degrees to approximately 40 degrees. In further embodiments, the curved planar member is substantially curved so as to match the contour of both the sacrum and the ilium.

FIG. 5A shows a lateral view of one embodiment of a curved planar member 500 having a tapered hole 503 for use in a SI joint implant. The curved planar member 500 has a first section 501 and a second section 502 residing on either side of an apex 504 of the curved planar member 500. In short, the shape of the curved planar member 500 is configured to substantially conform to the shape of the ilium and/or sacrum.

FIGS. 5B and 5C are two different embodiments of the curved planar member 500 of FIG. 5A. The embodiment depicted in FIG. 5B contains two or more tapered holes 503a and 503b (collectively 503), while the embodiment depicted in FIG. 5C contains only one tapered hole 503.

The embodiment illustrated in FIG. 5B has a curved planar member 500 having tapered holes 503 located in the second section 502 along a third longitudinal axis ad. The third longitudinal axis a, is analogous to the second longitudinal axis (apl, FIGS. 2A and 2B) of the planar member (200, FIGS. 2A-2C). To reduce slipping within the joint and thereby ensure that the curved planar member 500 remains in place following other manipulations, in some embodiments, the curved planar member 500 includes structural features 506 such as ridges, teeth, or other surface projections. One having ordinary skill will appreciate that the location and type of structural features will depend in inter alia, the joint involved, type of injury, and treatment desired.

In some instances, it is preferable to minimize the number of fastening elements required to affix the implant to the bone. For example, in cases where the patient's bone has reduced density due to osteoporosis, it may be advantageous to minimize the use of pre-drilled burholes to preserve bone integrity. FIG. 5C shows another embodiment of a curved planar member 500 having only one tapered hole 503. In this embodiment, a single tapered hole 503 is located along the third longitudinal axis ad of the second section 502 of the curved planar member 500. The first section 501 of the curved planar member 500 has surface modifications 506 to engage the ilium and prevent slipping of the implant.

b. Fixation Components

In operation, the SI joint implant is secured within the SI joint by one or more, typically two or more, fastening elements (601a and 601b, collectively 601) inserted through the tapered holes 201 of the planar member 200 to fixate the implant within the joint space. See FIG. 6. The fastening element is any suitable element for attaching a planar member 200 to a bone, such as a screw, nail, or rod. Preferably, the fastening elements are titanium bone screws. The bone screws can be of any standard type, but are preferably type HA. The bone screws can be self-tapping, cannulated, low-profile, hex-head, flat-head, or be of any other suitable type. In other embodiments, the fastening elements are made of any suitable biocompatible material, including non-biodegradable and biodegradable materials. In other embodiments the fastening elements are pins, rods, or other suitable structure for fixating the implant within the joint space.

c. Materials and Method of Manufacture of SI System

The various components of the SI implant system are fabricated from biocompatible materials suitable for implantation in a human body, including but not limited to, metals, synthetic polymers, ceramics, and/or their combinations, depending on the particular application and/or preference of a medical practitioner. Further, the components of the implant system can be manufactured via various methods. For example, the spacer or planer member may be manufactured and assembled via injection-molding, insert-molding, co-extrusion, pultrusion, transfer molding, overmolding, compression molding, 3-Dimensional printing, dip-coating, spray-coating, powder-coating, porous-coating, milling from a solid stock material and their combinations.

i. Spacer and Planar Member

The spacer 100 and planar member 200 can be fabricated from biocompatible materials such as commercially pure titanium, titanium alloys, Grade 5 titanium, super-elastic titanium alloys, cobalt-chrome alloys, stainless steel alloys, superelastic metallic alloys (e.g. nitinol, super elasto-plastic metals, such as GUM METAL™), carbon fiber, thermoplastics such as polyaryletherketone (PAEK), including polyetheretherketone (PEEK) and polyetherketone (PEK), carbon fiber reinforced PEEK composites, PEEK-BaSO4 composites, ceramics and composites thereof, such as calcium phosphate (e.g. SKELITE™), rigid polymers including polyphenylene, polyamide, polyimide polyetherimide, polyetherimide, polyethylene, polyurethanes of any durometer, epoxy, or silicone. Different components of the SI implant system may be fabricated from a heterogeneous material, such as a combination of two or more of the above described materials to achieve various desired characteristics such as strength, rigidity, elasticity, compliance, biomechanical performance, durability and radiolucency or imaging preference.

ii. Fixation and Assembly Elements

The fixation elements 601 and assembly elements 303 can be fabricated from biocompatible materials titanium, titanium alloys, Grade 5 titanium, super-elastic titanium alloys, cobalt-chrome alloys, stainless steel alloys, superelastic metallic alloys (e.g. nitinol, super elasto-plastic metals, such as GUM METAL™), stainless steel, carbon fiber or combinations thereof.

iii. Cavity Filler

In embodiments having a spacer cavity, the spacer cavity may be filled with suitable biocompatible materials to facilitate joint fixation or fusion. Suitable biocompatible materials include, but are not limited to bone material including autograft, allograft, xenograft or transgenic cortical and/or corticocancellous bone, and tissue growth or differentiation factors, partially resorbable materials, such as composite of metals and calcium based ceramics, composites of PEEK and calcium based ceramics, composites of PEEK with resorbable polymers, totally resorbable materials, such as calcium based ceramics such as calcium phosphate, tri-calcium phosphate (TCP), hydroxyapatite (HA)-TCP, calcium sulfate, or other resorbable polymers such as polylactide, polyglycolide, polytyrosine carbonate, and their combinations.

Figure 3:
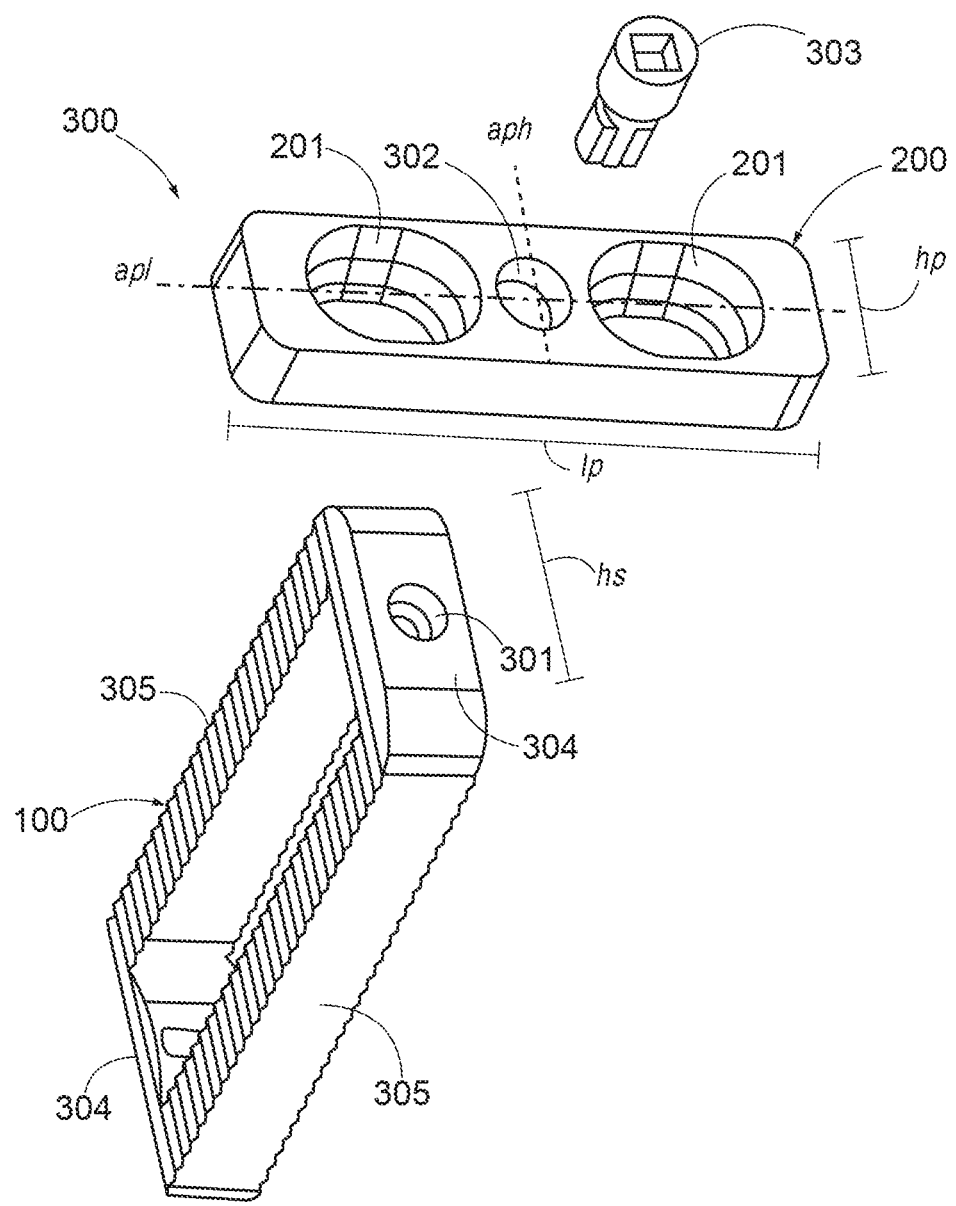
FIG. 3 shows one embodiment of a modular SI joint implant configured for in situ assembly.

II. Configuration of the SI Joint Implant System in Use a. Modular SI Joint Implant System FIG. 3 shows one embodiment of a modular SI joint implant configured for in situ assembly. For some SI joint procedures, it is preferable that the SI joint implant, which is a single unit in situ, be introduced to the joint one component at a time and operatively coupled together during the procedure to form the SI joint implant system. In situations when direct access to the SI joint is limited because small incisions are used, the ability to introduce components separately into the SI joint is particularly useful. In some embodiments, the SI joint implant is a modular implant system 300. The components of the modular SI joint implant system can be supplied as a kit.

During an implantation procedure of a spacer/planar implant, the medical practitioner inserts one component of the modular SI joint implant system 300 at a time into the SI joint and then operatively couples the spacer 100 to the planar member 200 in situ.

First, the spacer 100 is first delivered into the SI joint space. The spacer 100 is orientated such that the first assembly hole 301 is in a suitable position within the SI joint space to receive the assembly element 303. Then, the planar member 200 is delivered to the SI joint space and orientated such that the planar member 200 traverses the SI joint and the second assembly hole 302 aligns with the first assembly hole 301. The assembly element 303 is then passed through the second assembly hole 302 into the first assembly hole 301, thereby operatively coupling the planar member 200 and the spacer 100. When fully assembled in situ, the first longitudinal axis as of the spacer 100 is non-parallel, preferably substantially perpendicular, to the second longitudinal axis apl of the planar member 200. See e.g. FIG. 4B.

In further embodiments, the spacer 100 and the planar member 200 are not operatively coupled to one another in situ. The spacer 100 is inserted into the SI joint space and is held in place during the procedure by a suitable device. The planar member 200 is then placed in the SI joint, such that it traverses the SI joint. When fully fixed to the sacrum and the ilium it is expected that the planar member 200 will move the sacrum and ilium closer to one another, thus collapsing the SI joint space around the spacer 100. This compression of the SI joint space in these embodiments will be at least sufficient to hold the spacer 100 within the SI joint space until new bone growth in the SI joint space occurs.

b. Pre-Assembled SI Joint Implant System

There are also circumstances in which a pre-assembled implant system is desired. FIGS. 4A-4D show several views of one embodiment of an SI joint implant assembled ex vivo, i.e. assembled prior to implantation (referred to herein as "pre-assembled"). In one embodiment of a pre-assembled SI joint implant 400, the spacer 100 and the planar member 200 are operatively coupled at a joint 401 such that the first longitudinal axis as of the spacer 100 is non-parallel, preferably substantially perpendicular, to the second longitudinal axis apl of the planar member 200.

Preferably, the joint 401 is substantially centered along the horizontal axis aph of the planar member 200. See e.g. FIG. 4A. In other embodiments, especially in those in which the tapered holes 201 are staggered, the joint 401 can be at any position along the horizontal axis aph of the planar member 200. In all embodiments the joint 401 may be located at any position along the second longitudinal axis apl of the planar member that is not occupied by a tapered hole 201.

As shown in FIGS. 4C and 4D, preferably the joint 401 is formed from a joint fastener extending from the planar member 200 to a second receiver on the spacer 100. In further embodiments, the joint 401 is formed from a joint fastener extending from the spacer 100 to a first receiver on the planar member 200. In yet another embodiment, the joint 401 is formed by fusing the spacer 100 and the planar member 200 together, such that joint has no clear demarcation between the spacer 100 and the planar member 100. Thus, for these embodiments, the spacer 100 and the planar member 200 form one cohesive unit.

c. Curved SI Joint Implant

Figure 11A:
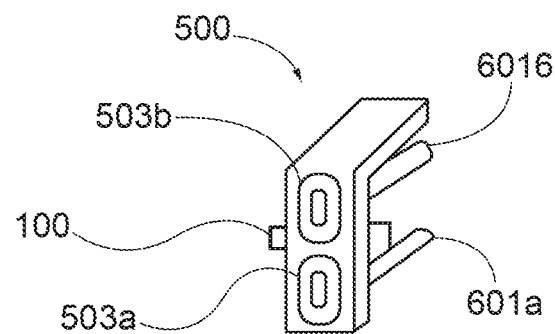
FIGS. 11A-11C show several views of one embodiment of a joint implant having a curved planar member and fixation elements placed through tapered holes in the curved planar member. For clarity, the implant is not shown within the SI joint.
Figure 11B:
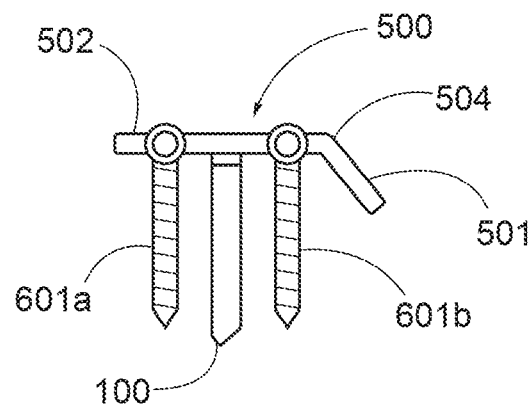
Figure 11C:
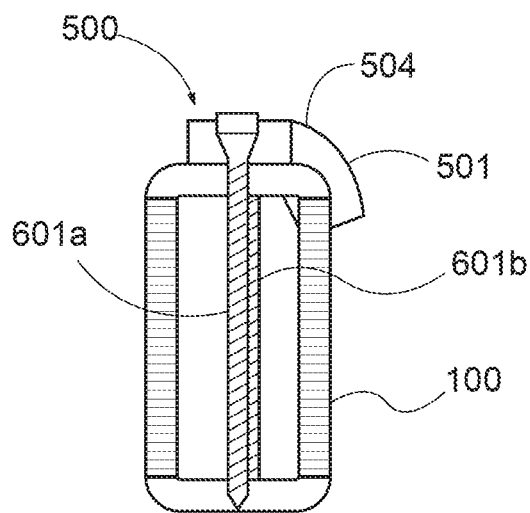
Figure 12:
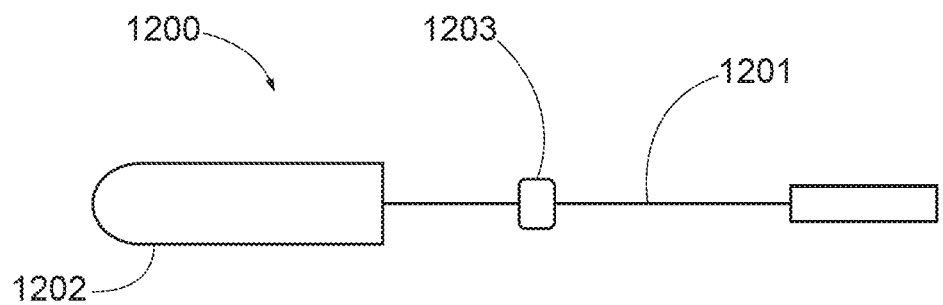
FIG. 12 shows one embodiment of a spatula for preparing the SI joint space.

Like the embodiments employing a straight planar member 200, embodiments of the SI joint implant system employing a curved planar member 500 can be modular or pre-assembled, as previously described. When the spacer 100 and curved planar member 500 are operatively coupled, the curved planar member 500 is oriented such that its longitudinal axis at is non-parallel, preferably substantially perpendicular, to the horizontal axis (ahp) of the spacer 100. See e.g. FIGS. 10A-10C. As shown in FIGS. 11A-11C, fixation elements 601 can be inserted through the tapered holes 503 of the curved planar member 500 and into the bones of the sacrum and ilium to secure the curved planar member 500 and spacer 100 within the SI joint.

III. Fixation of the SI Joint Implant within the SI Joint

In use, a fastening element 601 is placed through each tapered hole 201 into pre-drilled burholes in the bones of the patient's SI joint. These burholes are drilled off-center relative to the location of the corresponding tapered hole 201. As the fastening element is inserted within the bone of a patient (e.g. when a screw is being tightened), the tapering of the tapered hole 201 forces the fastening element 601 to move from an initial position to a final position that is substantially displaced from the initial position and towards the spacer 100, preferably resulting in compression of the SI joint space. This action is sometimes referred to as dynamic compression. This process is discussed in greater detail with reference to FIGS. 6A-7D.

Methods of stabilizing the SI joint employing rods, screws, or other devices that are inserted laterally through the hip and traverse the SI joint do not typically induce significant bone growth across the SI joint space so as to fuse the joint. Here, the SI joint implant promotes significant bone growth across the SI joint so as to result in fusion of the joint as opposed to merely stabilization. Any compression provided by the action of the fastening element 601 within the planar member 200 further promotes in new bone growth across the SI joint and further stabilizes the SI joint.

a. Initial Position of Fixation Components

Figure 6A:
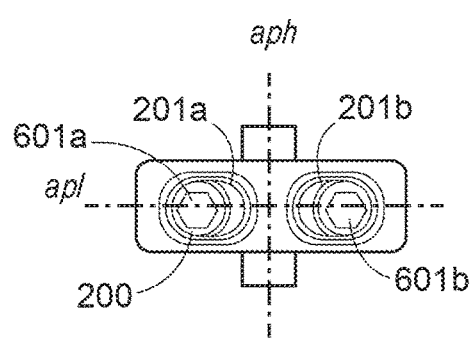
FIGS. 6A-6D show several views of one embodiment of a joint implant prior to affixing the SI implant within the SI joint. For clarity, the implant is not shown within the SI joint.
Figure 6B:
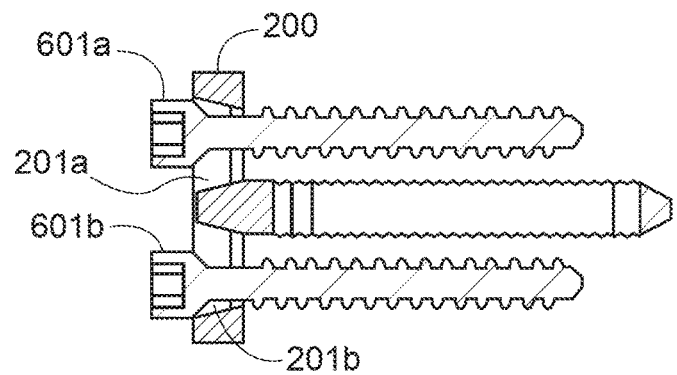

FIGS. 6A-6D illustrate one embodiment of a fully assembled SI joint implant prior to affixing the SI implant within the SI joint. Turning first to FIGS. 6A and 6B, the method of fixing the SI joint implant within the SI joint begins by first inserting fastening elements 601 through the tapered holes 201 into pre-drilled boreholes in the patient's bone. The boreholes are placed in the patient's bone such that they are substantially off-center relative to the location of the corresponding tapered holes 201 (503) of the planar member 200 (curved planar member 500). Preferably, the location of the boreholes, relative to the tapered holes 201, is distal to the spacer 100 or second assembly hole (FIG. 3, 302). Thus, when the fastening elements 601 are initially placed through the tapered holes 201 (503) into the boreholes, the fastening elements 601 are off-center within the tapered holes 201 (503) of the planar member 200 (curved planar member 500). See e.g. FIGS. 6A-6B.

Figure 6C:
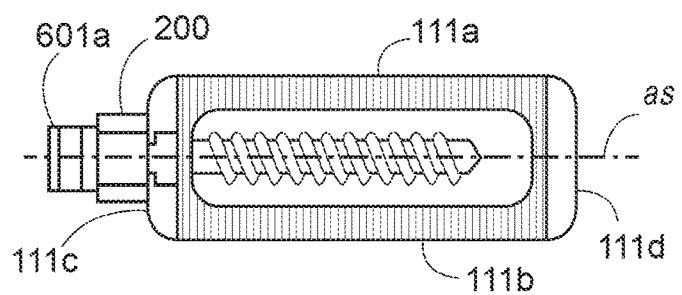
Figure 6D:
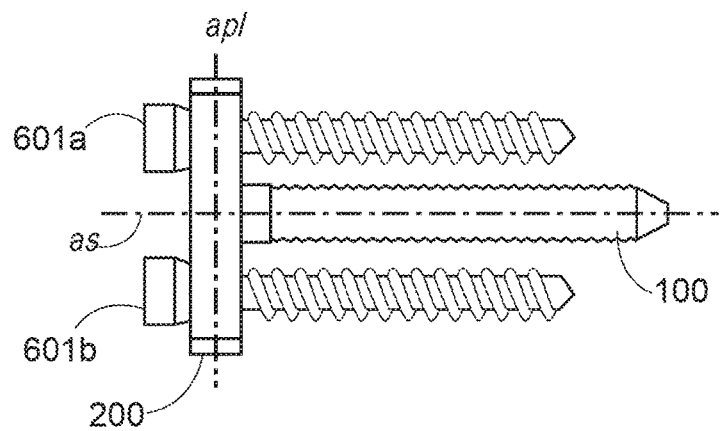

As illustrated in FIGS. 6B through 6D, the fastening elements 601 are preferably positioned such that they are substantially parallel to the spacer 100. However, the fastening elements 601 can have any angle the medical practitioner deems necessary or prefers. One having ordinary skill will appreciate that this will depend on, inter alia, the joint involved, type of injury, and treatment desired.

The holes for the screws can be prepared with the conventional steps of: perforating the cortical bone, for example using an awl or burr; drilling the bone to create a screw trajectory for the tap; tapping the bone as deep as needed to help drive the screw; and implanting the screws.

b. Final Position of Fixation Components

Figure 7A:
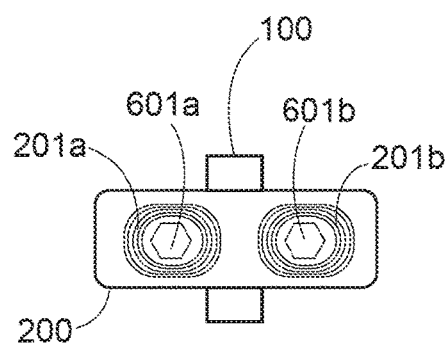
FIGS. 7A-7D show several views of one embodiment of a joint implant after affixing the SI implant within the SI joint. For clarity, the implant is not shown within the SI joint.
Figure 7B:
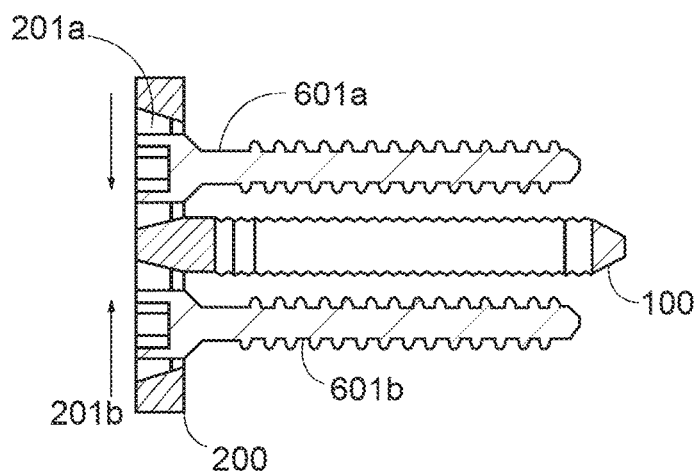
Figure 7C:
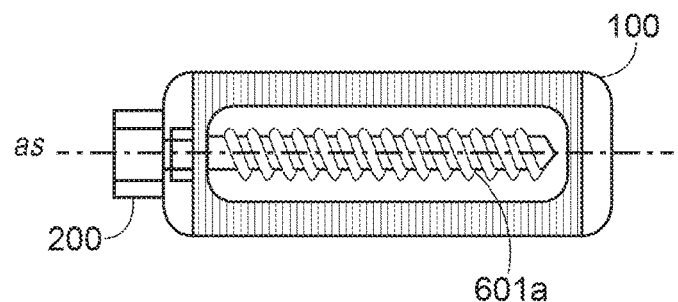
Figure 7D:
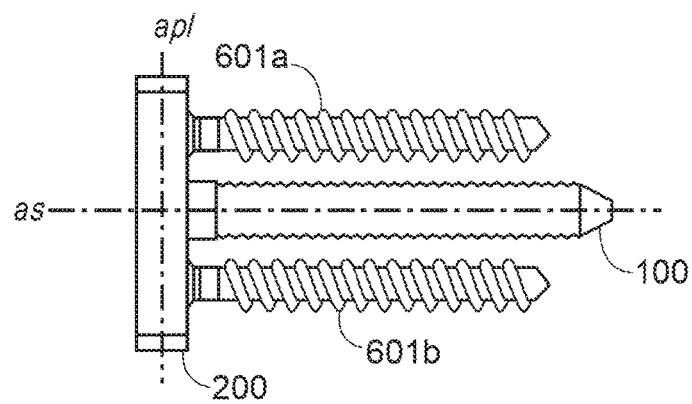

The final position of the fastening elements 601 is depicted in FIGS. 7A-7D. In use, the medical practitioner completely inserts, or sets, the fastening elements 601 in the bones of the SI joint. As the fastening elements 601 are finally set into the bone, they move from their initial position (illustrated, e.g., in FIGS. 6A and 6B) within the tapered holes 201 to their final position, which is preferably substantially centered within the tapered holes 201. This final configuration is shown in FIGS. 7A and 7B. Thus, as the fastening elements 601 are set into the bone, the taper of the tapered holes 201 forces the fastening elements 601 into a final position that is closer to the joint space, moving the fastening elements 601 closer together.

IV. SI Joint Implant Delivery

Figure 8:
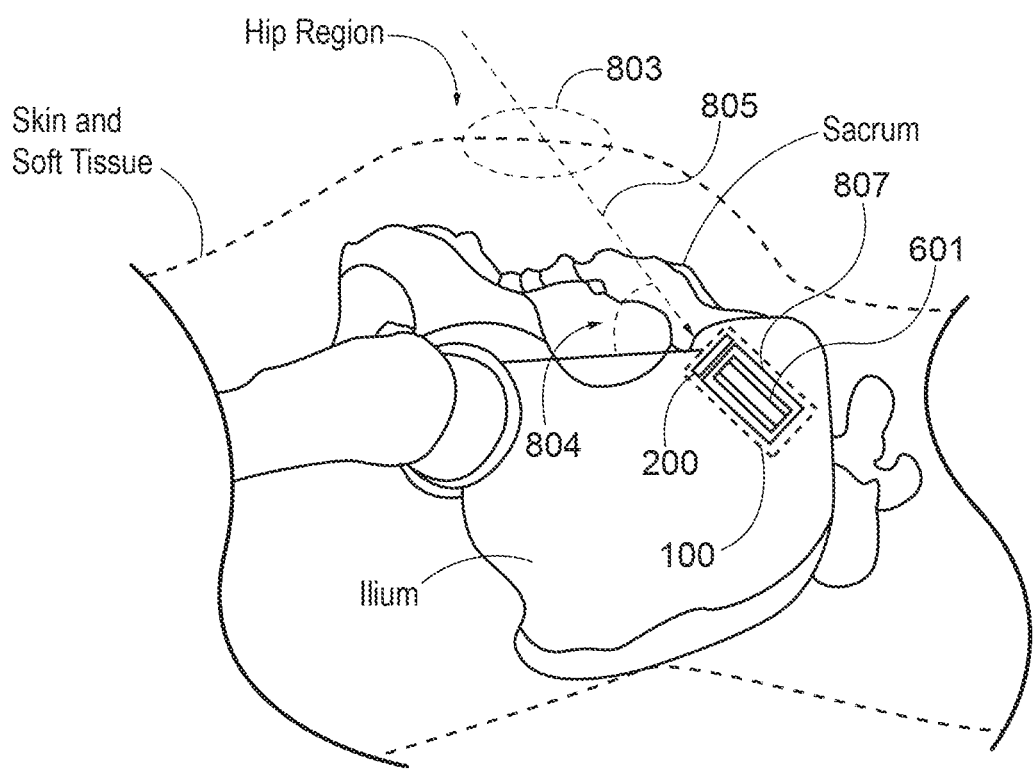
FIG. 8 shows a lateral view of a hip region illustrating an approximate location of a SI joint implant within the SI joint.

The inferior inlet approach disclosed herein may be used to deliver any SI joint implant or other device to the SI joint or SI joint region. Preferably, the inferior inlet approach is used to deliver the SI joint implants disclosed herein to an SI joint of a patient in need thereof. FIG. 8 shows a lateral view of a hip region illustrating an approximate location of an SI joint implant within the SI joint.

For delivery of the SI joint implant, the patient is preferably placed in a prone position. If desired, fluoroscopy is used to visualize the SI joint according to methods well established in the field. Preferably, the position of the fluoroscopy is an inlet view of the pelvis with an approximately 10-15 degree angle to isolate the affected SI joint. This view provides a medical practitioner with a straight view of the SI joint.

A medical practitioner then accesses the SI joint through an incision in the skin and soft tissue of a patient. The incision may be of any size, but preferably the incision is less than one inch. The incision is made in a region 803 below the back of a patient. Preferably, the incision is made in alignment with the longitudinal axis of the SI joint. The angle 804 of a trajectory 805 of the inferior inlet approach is less than 90 degrees.

After the incision is made, a guide wire, such as a K-wire, is inserted through the incision and advanced until it reaches the SI joint. The guide wire is used to guide the surgical instruments to the desired site.

Optionally, one or more dilators are fed along the K-wire to push soft tissue aside. For example, a dilation system having a plurality of tubular members that can be concentrically disposed may be used. First, a smallest first tubular member is fed over the guide wire so that a distal end of the first tubular member is advanced into the surgical site. As the distal end advances into the incision, the tissue surrounding the first tubular member is radially outwardly retracted or dilated.

Once the first tubular member is inserted to a desired depth, a slightly larger second tubular member is pushed over the second tubular member and into the tissue so as to further dilate the tissue. This process is repeated for additionally larger tubular members until the tissue at the surgical site is retracted to a desired extent to facilitate the surgical procedure.

After reaching the desired width, all of the inner dilators are removed, while the outermost tubular member (dilator) remains in place, defining the opening through which the other surgical instruments will be inserted.

The various instruments that are used to prepare the SI joint increase in width, with the smallest instrument used initially and the largest instrument used prior to insertion of the SI joint implant. For example, for an implant that is 6 mm in width, the instruments may progressively increase in width starting with an instrument of about 3 mm in width and ending with an instrument that is about 5.75 mm in width, this allows for a press fit (or friction fit) of the implant to the bone after preparation of the SI joint.

A spatula 1200 having a handle 1201 and a spatula end 1202 is placed within the incision and fed along the guide wire into the inferior aspect of the SI joint in alignment with the longitudinal axis of the SI joint. In one embodiment, the handle is removed. The spatula may have any suitable dimensions, but preferably is approximately 20-30 mm in length, 15-20 mm in height, and about 3-4 mm in width, preferably 3.5 mm in width. Preferably, the spatula 1200 has a stop 1203 placed in a suitable location to prevent over insertion of the spatula 1200 within the SI joint. Preferably, the spatula has a suitable configuration to guide the box chisel over the shaft of the spatula and prevent rotation of the box chisel relative to the spatula. Typically, the shaft of the spatula is rectangular.

Figure 13:
FIG. 13 shows one embodiment of a box chisel for preparing the SI joint space.
Figure 14:
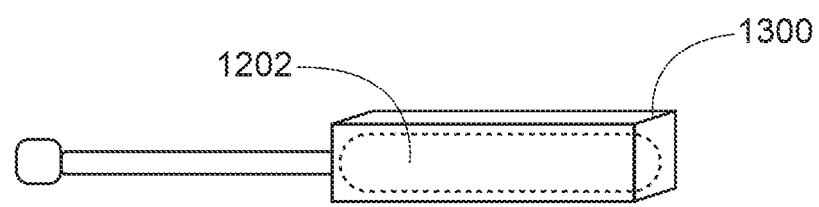
FIG. 14 shows the spatula of FIG. 12, with a handle removed, inside the box chisel of FIG. 13, as would occur during preparation of the SI joint space.

Once the spatula 1200 is placed within the SI joint, the removable handle 1201 is detached, leaving the spatula end 1202 and the stop 1203, if present, at the inferior aspect (FIG. 16, 1500) of an SI joint. As shown in FIGS. 13 and 14, a box chisel 1300 is then placed over the spatula end 1202. The box chisel preferably includes a hollow portion along the length of the chisel, which mates with the configuration of the shaft of the spatula. This allows the chisel to slide along the length of the spatula without rotation to the desired site. The chisel has suitable dimensions for fitting in the SI joint. Typically, the tip of the chisel has a width of about 5-6 mm, preferably 5.5 mm. Preferably, the chisel also contains a window (or opening) at its proximal tip region. This opening is configured for graft retrieval.

The box chisel is then manipulated by the surgeon to remove cartilaginous/fibrous tissue on either side of the SI joint. This results in a suitable environment for bone growth to promote fusion of the SI joint. Using this combination of the spatula 1200 and the box chisel 1300 as described herein, results in equal thickness of joint space on either side of the spatula.

It may be difficult to remove the box chisel from the SI joint. Optionally a mallet or slap hammer is used to apply an impacting force on the box chisel and loosen it from the site to aid in its removal. Optionally, the distal end of the box chisel is configured for attachment to a slap hammer.

Slap hammers typically consist of a guide rod and a sliding weight. One end of the guide rod is affixed to an object or surface, such as a box chisel (or any other surgical tool that requires removal). The sliding weight may be thrown upward, generating a jerking force when the sliding weight strikes a stop on the end of the guide rod. The sliding weight may be repeatedly "thrown" to extract the surgical implement.

Figure 15:
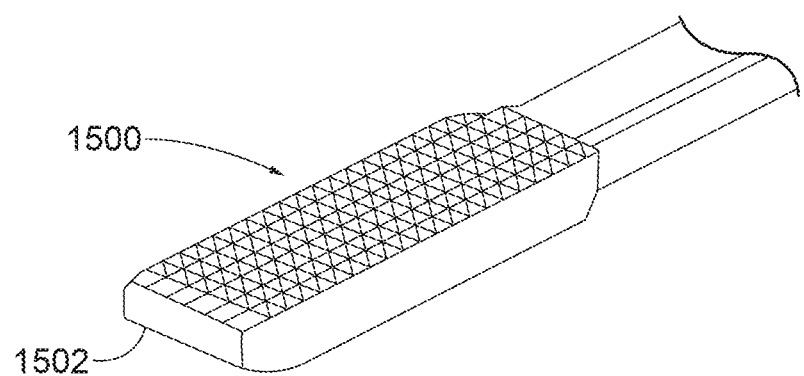
FIG. 15 shows one embodiment of a rasp for roughening the bone surface.

If desired, a rasp, or other suitable device, can be used for additional preparation of the SI joint space. The rasp may be used to roughen the bone surface to prepare for fusion. An exemplary rasp 1500 is illustrated in FIG. 15. Typically, the tip 1502 of the rasp has a width of about 5-6 mm, preferably 5.75 mm. Optionally, the distal end of the rasp is configured to attach to a slap hammer.

Optionally, loose debris within the SI joint space is removed. For example, pituitary ronguer, or other suitable device, may be used to remove loose debris from the SI joint prior to insertion of the SI joint implant.

Preferably, the prepared SI joint space resulting from use of the box chisel 1300 and other optional devices is approximately 2 mm smaller than the width of the spacer 100. This provides a press-fit and distraction of the SI joint leading to further stabilization of the SI joint by reducing micromotion. The prepared SI joint space is at least the length of the spacer 100.

a. Delivery of a Modular SI Joint Implant

Figure 16:
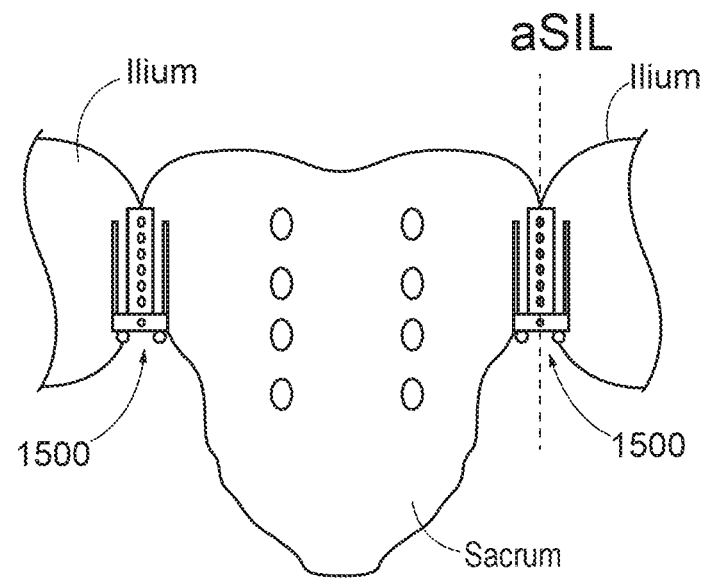
FIG. 16 is a posterior view showing the SI joint implants within the SI joints.
Figure 17:
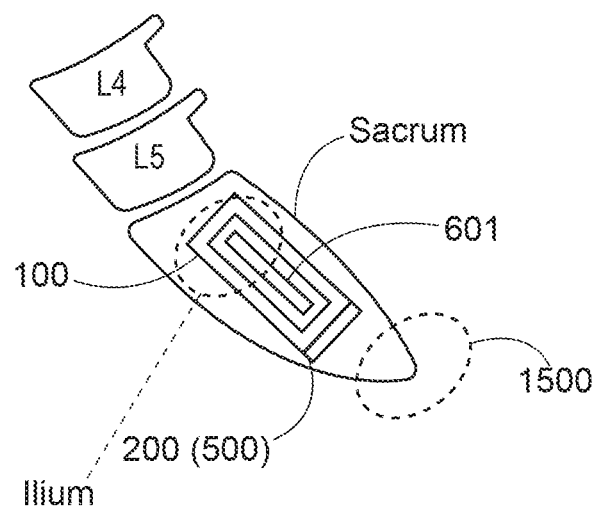
FIG. 17 is a lateral view showing the approximate location of the SI joint implant within the SI joint relative to the sacrum and spine.

For a modular SI joint implant 300, the spacer 100 is inserted within the prepared SI joint space at the inferior aspect 1500 of the SI joint, such that the spacer 100 engages the articular surfaces of the SI joint. See e.g. FIG. 16. This is followed by placement of the planar member 200 (or 500) along the inferior aspect 1500 of the SI joint as shown in FIG. 16. Fixation elements 601 are then inserted through the tapered hole or holes 503 in the planar member 200 (or 500). The fixation elements 601 are inserted along the longitudinal axis of the SI joint (asIl) without encroaching on the neural foramen of the sacrum, as shown in FIG. 16. In some embodiments, the planar member 200 (or 500) is operatively coupled to the spacer 100 via the assembly element as previously described prior to insertion of the fixation elements through the tapered holes 503. In other embodiments, coupling of the planar member 200 (or 500) and the spacer 100 via the assembly element 303 occurs after the fixation elements 601 have been inserted through the tapered holes 303 into the bones. In other embodiments, the spacer 100 and planar member 200 (or 500) are not operatively coupled together, as previously described. In these embodiments, the spacer 100 is held within the SI joint space by the press-fit of the spacer 100 within the SI joint space and/or compression on the SI joint space provided by the dynamic compression action of the planar member 200 (or 500).

b. Delivery of a Pre-Assembled SI Joint Implant

For the pre-assembled SI joint implant, the pre-assembled SI joint implant is delivered to the prepared SI joint space, such that the spacer 100 is within the SI joint space, and the planar member 200, 500 traverses the SI joint along the inferior aspect 1500 of the SI joint. See e.g. FIGS. 15 and 17. Fixation elements 601 are then inserted through the tapered hole(s) 503 of the planar member 200, 500 and into the bones. The fixation elements 601 are inserted such that they are aligned with the longitudinal axis of the SI joint without encroaching on the neural foramen of the sacrum.

The inferior inlet approach provides access to the inferior aspect 1500 of the SI joint while avoiding the nerves exiting the sacrum, as well as the majority of blood vessels, ligaments, and muscles supporting the hip and lumbar region of a patient. Further, the inferior inlet approach allows for smaller incisions than the current MIS techniques for accessing the SI joint. Therefore, the inferior inlet approach reduces recovery time, risk of complications from surgery, and reduces visibility of the incision once healed.

Figure 9:
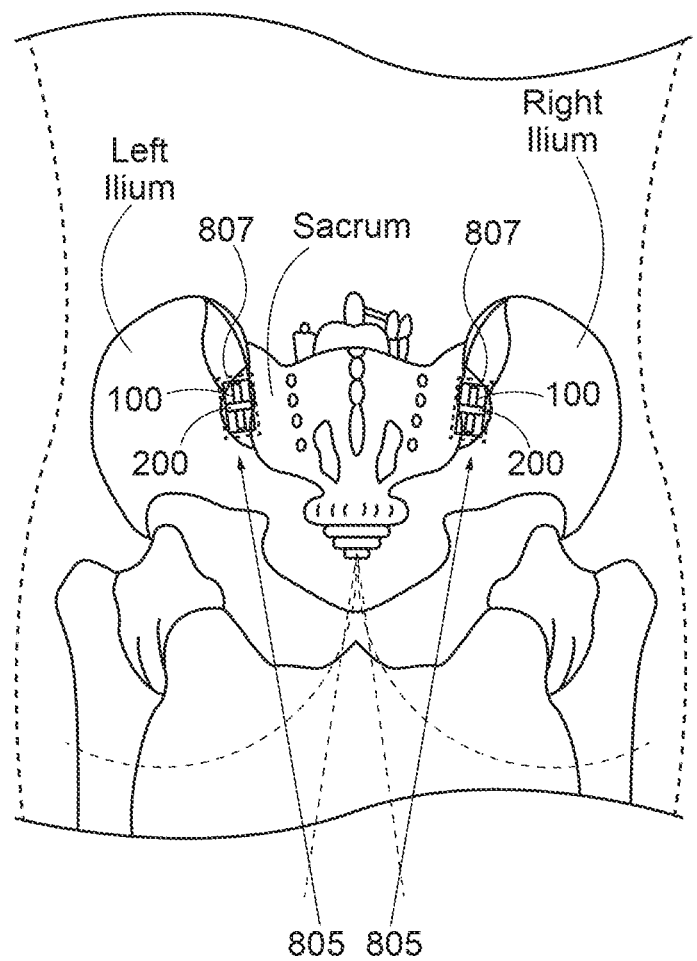
FIG. 9 shows a posterior view of the hip region illustrating an approximate location of a SI joint implant within the SI joint.
Figure 10A:
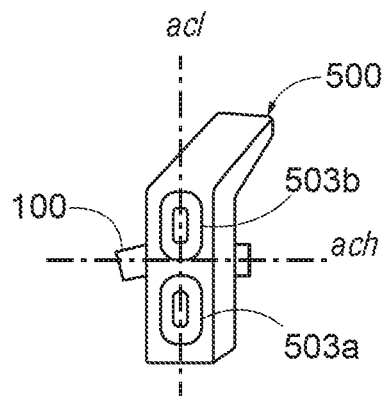
FIGS. 10A-10C show several views of one embodiment of a joint implant having a curved planar member. For clarity, the implant is not shown within the SI joint.
Figure 10B:
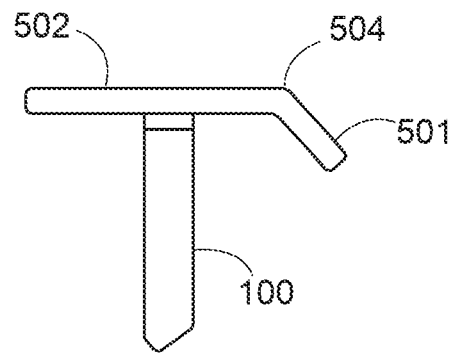
Figure 10C:
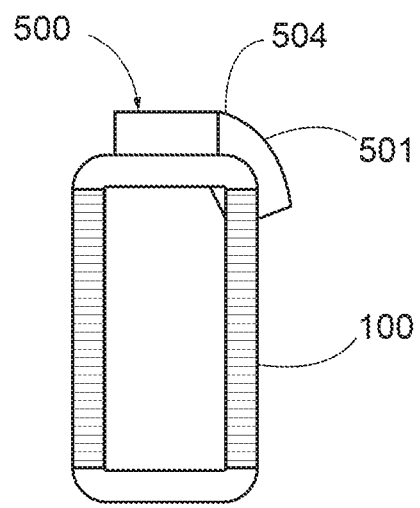

FIG. 9 shows a posterior view of the hip region illustrating an approximate location of a SI joint implant within the SI joint. As illustrated in FIG. 9, the trajectory 805 of the inferior inlet approach allows key elements of the vascular, nervous, and musculoskeletal system to be avoided. In one embodiment, the SI joint implant is placed or assembled within the prepared SI joint space 807 at the inferior aspect 1500 of the SI joint, such that the spacer 100 engages the surface of the sacrum and the ilium. Moreover, the planar member 200 (or 500) traverses the SI joint such that the implant may be affixed to the sacrum and the ilium through the tapered holes 201 as previously described. The alignment of the SI joint implant at the inferior aspect 1500 of the SI joint is shown in greater detail with respect to the sacrum and spinal column in FIG. 17.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain, using no more than routine experimentation, many equivalents to the specific embodiments of the invention described herein. Such equivalents are intended to be encompassed by the following claims.

The invention claimed is:

1. A system for fusing a sacroiliac (SI) joint, comprising:
a box chisel having a proximal end and a distal tip opposite the proximal end along an instrument axis, the box chisel being cannulated and configured to be inserted along an inferior insertion direction to prepare the SI joint, wherein the inferior insertion direction is offset inferiorly with respect to a posterior-anterior direction that is perpendicular a superior-inferior direction;
an implant body configured for engagement with articular surfaces of the SI joint via an inferior insertion direction, the implant body being elongated along a first longitudinal axis and having a first end, a second end opposite the first end along the first longitudinal axis, a first surface coupled to the first end and the second end, a second surface opposite the first surface and coupled to the first end and the second end, a first side surface coupled to the first end and the second end, a second side surface opposite the first side surface and coupled to the first end and a second end, and a cavity that extends entirely through the implant body, the implant body defining a length that extends from the first end to the second end, a width that extends from the first surface to the second surface and that is perpendicular to the length, and a height that is perpendicular to the length and the width, wherein the length is greater than the width and the height; and
a spatula having a handle, a shaft that extends from the handle in a distal direction, a spatula end coupled to the shaft, and a stop positioned in a proximal direction relative to the spatula end in the distal direction, wherein the stop is positioned to prevent over insertion of the spatula within the SI joint, wherein the spatula is configured to guide the box chisel over the shaft of the spatula;
wherein the distal tip is configured to engage the articular surfaces of the SI joint along the inferior insertion direction to define a space for receiving the implant body.

2. The system of claim 1, wherein the distal tip defines a tip width that intersects and is perpendicular to the instrument axis, wherein the width of the implant body is greater than the tip width such that implant body creates an interference fit in the SI joint when the implant body is placed in the space of the SI joint.

3. The system of claim 2, wherein the tip width of the box chisel is at least 2 mm smaller than the width of the implant body.

4. The system of claim 2, wherein the tip width is between 5 mm and 6 mm.

5. The system of claim 1, wherein the handle is removable from the spatula to permit the box chisel to be placed over the shaft.

6. The system of claim 1, further comprising a plurality of dilators configured to prepare tissue proximal to the SI joint.

7. The system of claim 1, wherein the implant body has four implant body edges that define the cavity, wherein each edge defines a thickness that is substantially equal to one another.

8. The system of claim 7, wherein the first end defines a tapered edge, wherein the tapered edges has ridges and one or more of the first surface and the second surface has ridges.

9. The system of claim 1, wherein the length of the implant body is between about 30 mm to about 50 mm, the height of the implant body is between about 15 to about 25 mm, and the width of the implant body is between about 6 mm and about 8 mm.

10. The system of claim 1, further comprising:
a first fastener configured to engage a first bone location proximate the SI joint; and
a second fastener configured to engage a second bone location proximate the SI joint, wherein the first and second fasteners are configured to engage the bone so that 1) the implant body is positioned between the first fastener and the second fastener, and 2) the first and second fastener are substantially parallel to the length of the implant body.

11. The system of claim 1, wherein the spatula is configured to prevent rotation of the box chisel relative to the spatula.

12. A system for fusing a sacroiliac (SI) joint, comprising:
at least one instrument configured to be inserted along an inferior insertion direction to prepare the SI joint, wherein the inferior insertion is offset inferiorly with respect to a posterior-anterior direction that is perpendicular to a superior-inferior direction;
an implant body configured to engage articular surfaces of the SI joint via an inferior insertion direction, the implant body being elongated along a first longitudinal axis and having a first end, a second end opposite the first end along the first longitudinal axis, a first surface coupled to the first end and the second end, a second surface opposite the first surface and coupled to the first end and the second end, and a cavity that extends from the first surface to the second surface, the implant body defining a length that extends from the first end to the second end, a width that extends from the first surface to the second surface and that is perpendicular to the length, and a height that is perpendicular to the length and the width;
a first fastener configured to engage a first bone location proximate the SI joint;
a second fastener configured to engage a second bone location proximate the SI joint, wherein the first and second fasteners are configured to engage the bone so that 1) the implant body is positioned between the first fastener and the second fastener, and 2) the first and second fastener are substantially parallel to the length of the implant body; and
a spatula having a handle, a shaft that extends from the handle in a distal direction, a spatula end coupled to the shaft, and a stop positioned in a proximal direction relative to the spatula end in the distal direction, wherein the stop is positioned to prevent over insertion of the spatula within the SI joint, wherein the spatula is configured to guide the at least one instrument over the shaft of the spatula and prevent rotation of the at least one instrument relative to the spatula;
wherein the at least one instrument is a box chisel having a proximal end and a distal tip opposite the proximal end along an instrument axis, the distal tip configured to engage the articular surfaces of the SI joint along the inferior insertion direction to define a space for receiving the implant body, the distal tip defining a tip width that intersects and is perpendicular to the instrument axis, wherein the width of the implant body is greater than the tip width such that the implant body creates an interference fit in the SI joint when the implant body is placed in the space of the SI joint;
wherein a proximal head of the first and second fasteners are aligned along a plane that intersects a proximal end of the implant body.

13. The system of claim 12, wherein the tip width of the at least one instrument is at least 2 mm smaller than the width of the implant body.

14. The system of claim 12, wherein the tip width is between 5 mm and 6 mm.

15. The system of claim 12, wherein the box chisel is cannulated.

16. The system of claim 12, wherein the handle is removable from the spatula to permit the box chisel to be placed over the shaft.

17. The system of claim 12, wherein the first and second fasteners substantially traverse an entire length of the implant body.

18. The system of claim 12, wherein the length and the height are substantially equal.

* * * * *